US00PP36409P2

(12) United States Plant Patent
Fieldes

(10) Patent No.: US PP36,409 P2
(45) Date of Patent: Jan. 21, 2025

(54) ***SENECIO* PLANT NAMED 'Angel Baby'**

(50) Latin Name: *Senecio candidans*
Varietal Denomination: Angel Baby

(71) Applicant: Flowerzone International Ltd, Auckland (NZ)

(72) Inventor: Lyall Fieldes, Whangerei (NZ)

(73) Assignee: FLOWIERZONE INTERNATIONAL LTD, Auckland (NZ)

( * ) Notice: Subject to any disclaimer, the term of this patent is extended or adjusted under 35 U.S.C. 154(b) by 0 days.

(21) Appl. No.: 18/640,080

(22) Filed: Apr. 19, 2024

(30) Foreign Application Priority Data

Jan. 8, 2024 (QZ) ..... PBR 20240021

(51) Int. Cl.
*A01H 5/12* (2018.01)
*A01H 6/14* (2018.01)

(52) U.S. Cl.
USPC ..... Plt./480

(58) Field of Classification Search
USPC ..... Plt./480
CPC ..... A01H 5/12; A01H 5/00; A01H 6/14
See application file for complete search history.

*Primary Examiner* — June Hwu
(74) *Attorney, Agent, or Firm* — Penny J. Aguirre

(57) ABSTRACT

A new cultivar of *Senecio* plant named 'Angel Baby' that is characterized by its compact plant habit (15 to 20 cm in height and spread), its leaves that are silvery white in color and blushed with green and become more green with age, and its leaves that are oval in shape and slightly curly.

2 Drawing Sheets

CROSS-REFERENCE TO RELATED APPLICATIONS

This application claims priority to European Community Plant Variety Office (CPVO) Plant Breeder's Rights application No. 2024/0021 filed on Jan. 8, 2024, under 35U.S.C. 119 (f), the entire contents of which is incorporated by reference herein. The Applicant received the information for the Plant breeders' rights application directly from the Inventor. This application is co-pending with a U.S. Plant Patent application filed for a plant derived from the same breeding program that is entitled *Senecio* Plant Named 'Sennova Mi RL' (U.S. Plant Patent application Ser. No. 18/640,104).

Botanical classification: *Senecio candidans.*

Variety denomination: 'Angel Baby'.

BACKGROUND OF THE INVENTION

The present invention relates to a new and distinct cultivar of *Senecio* plant, botanically known as *Senecio candidans* 'Angel Baby' and will be referred to hereafter by its cultivar name, 'Angel Baby'. The new cultivar represents a new sea cabbage grown as an ornamental used for landscape and container use.

The Inventor discovered the new cultivar in summer of 2020 as a naturally occurring branch mutation of *Senecio* 'Angel Wings' (not patented) that was growing in a greenhouse in a container in Hachimantai, Iwate, Japan.

Asexual propagation of the new cultivar was first accomplished by stem cuttings in Hachimantai, Iwate, Japan in April of 2021 by the Inventor. Asexual propagation by stem cuttings and tissue culture using meristemaic tissue has determined that the characteristics of this cultivar are stable and are reproduced true to type in successive generations.

SUMMARY OF THE INVENTION

The following traits have been repeatedly observed and represent the characteristics of 'Angel Baby'. These attributes in combination distinguish 'Angel Baby' as a new and distinct cultivar of *Senecio.*

1. 'Angel Baby' exhibits a compact plant habit (15 to 20 cm in height and spread).
2. 'Angel Baby' exhibits leaves that are silvery white in color and blushed with green and become more green with age.
3. 'Angel Baby' exhibits leaves that are oval in shape and slightly curly.

The parent plant of 'Angel Baby' differs from 'Angel Baby' in having a less compact plant habit and leaves that are round to cordate in shape that are more silvery white in color. 'Angel Baby' can also be compared to cultivars *Senecio niveoaureus* 'Silver Feathers' (not patented) and *Senecio candidans* 'Sennova Mi RL'.'Silver Feathers' is similar to 'Angel Baby' in having silver foliage that is densely covered with woolly pubescent hairs. 'Silver Feathers' differs from 'Angel Baby' in having leaves that are more linear in shape, become limp, and are less thick. 'Sennova Mi RL' is similar to 'Angel Baby' in having foliage that is silvery white and green in color and densely covered with woolly pubescent hairs. 'Sennova Mi RL' differs from 'Angel Baby' in having a slightly larger plant size and leaves that are broadly ovate to broadly oblong in shape and less curly.

BRIEF DESCRIPTION OF THE DRAWINGS

The accompanying color photographs illustrates the overall appearance and distinct characteristics of the new *Senecio*. The photographs were taken of a 1-year-old plant of 'Angel Baby' as grown in an unheated conventional greenhouse in a 15-cm container in Berkel en Rodenrijs, The Netherlands.

The photograph in FIG. 1 provides a side view of a plant of 'Angel Baby'.

Figure 1:
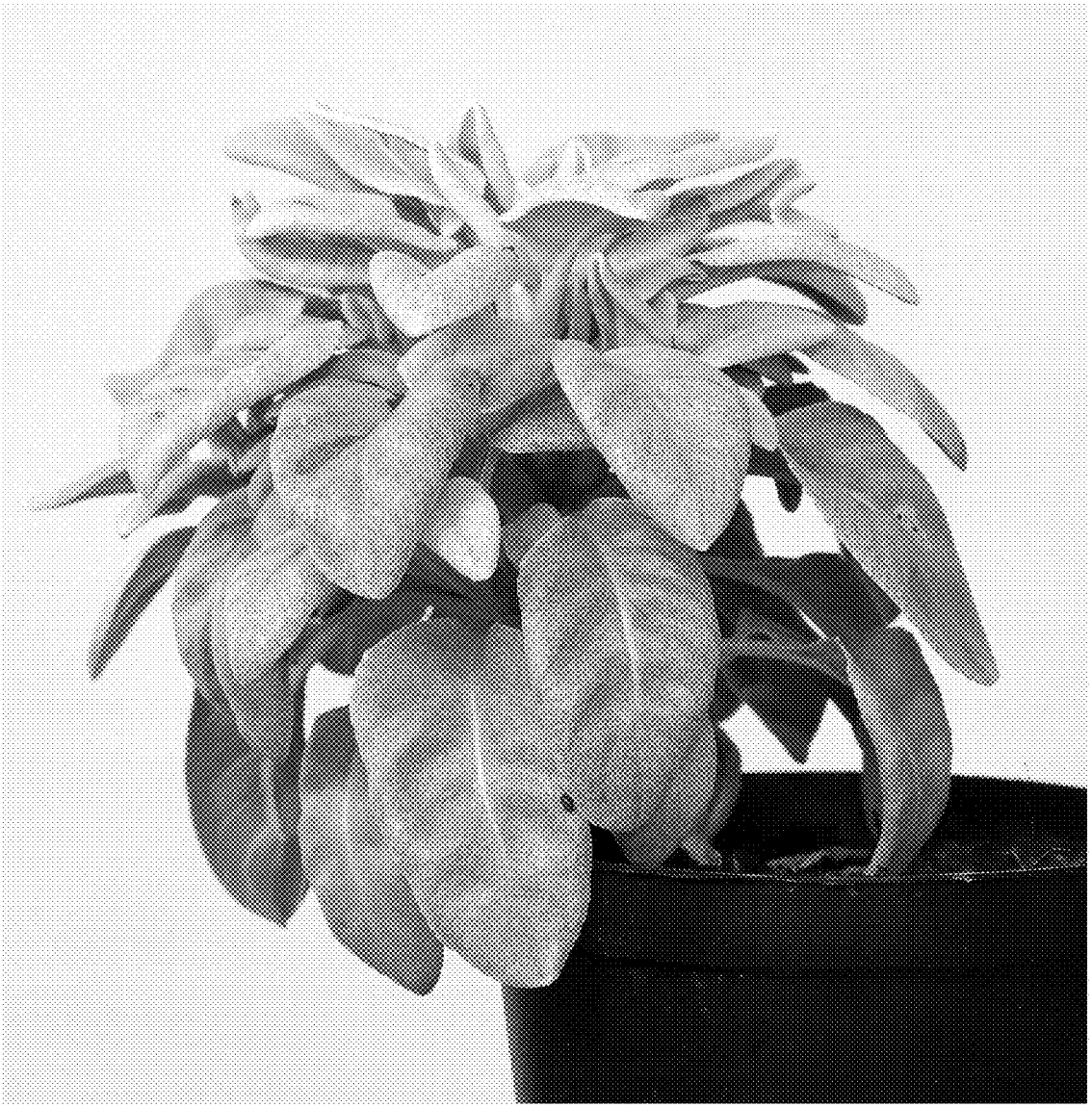
Figure 2:
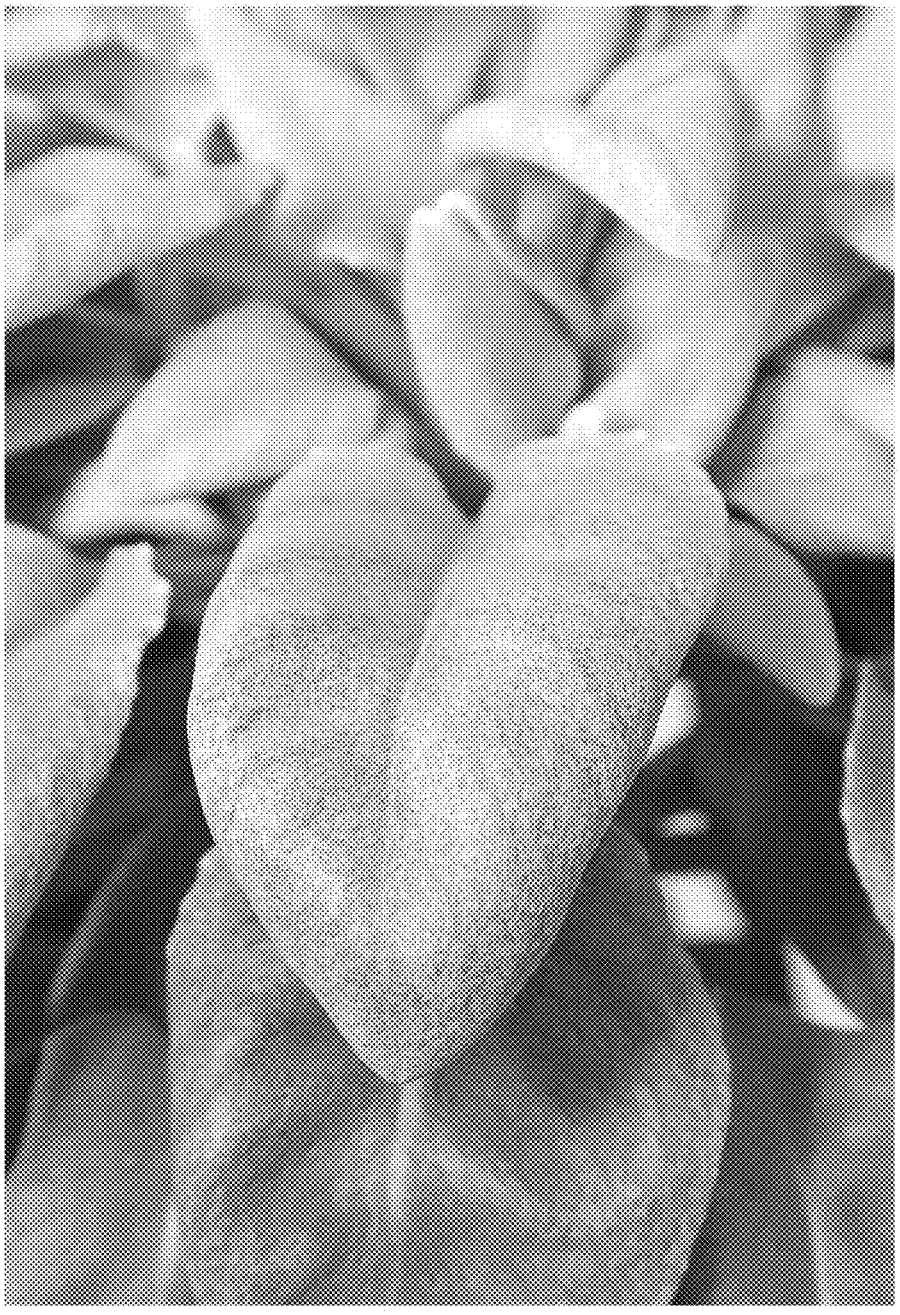

The photograph in FIG. 2 is a close-up view of the foliage of 'Angel Baby'.

The colors in the photographs may differ slightly from the color values cited in the detailed botanical description, which accurately describe the colors of the new *Senecio*.

DETAILED BOTANICAL DESCRIPTION

The following is a detailed description of 1-year-old plants of the new cultivar as grown in 15-cm containers in a conventional unheated greenhouse in Berkel en Rodenrijs, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Plant type*.—Evergreen perennial.

*Plant habit*.—Compact, globular and broadly spreading.

*Height and spread*.—An average of 16.5 cm in height and 19.4 cm in width as a one-year-old plant grown in a container, reaches 15 to 20 cm in height and width when grown in the landscape.

*Hardiness*.—At least to U.S.D.A. Zones 8 to 11.

*Diseases and Pests*.—No susceptibility or resistance to diseases or pests has been observed.

*Root description*.—Fibrous.

*Propagation*.—Stem cuttings and tissue culture.

*Time required for root development*.—An average of 2 to 4 weeks for root initiation and 3 to 5 months to fully root as a young plant.

*Growth rate*.—Moderately vigorous.

Stem description:

*Stem shape*.—Rounded.

*Stem color*.—146D.

*Stem size*.—Average of 4.4 cm in length and 5 mm in diameter.

*Stem surface*.—Matte, densely covered with woolly pubescence 192D in color.

*Branching*.—Main; 1, lateral branches; 7.

*Aspect*.—Main; 70° from horizontal, lateral; 30° to main.

*Internode length*.—Average of 6 mm.

Foliage description:

*Leaf division*.—Simple.

*Leaf arrangement*.—Alternate.

*Leaf shape*.—Oval.

*Leaf size*.—Average of 7.4 cm in length and 5.2 cm in width.

*Leaf number*.—Average of 6 per lateral branch.

*Leaf base*.—Broad attenuate.

*Leaf apex*.—Obtuse to bluntly acute.

*Leaf margin*.—Entire; lower half to lower ⅓rd shallow dentate, with blunt teeth, margin strongly revolute, undulation low to none.

*Leaf aspect*.—Moderate to strongly convex and slightly curly.

*Leaf venation*.—Pinnate, upper veins color; 146B, densely covered with woolly pubescent hairs 192D in color, lower veins color; 194B, densely covered with woolly pubescent hairs 192D.

*Leaf color*.—Young upper surface; 137C, densely covered with woolly pubescent hairs a blend of N155A and 192D, young lower surface; NN137B, densely covered with woolly pubescent hairs a blend of N155A and 192D, mature upper surface; 144A, densely covered with woolly pubescent hairs 192D, mature lower surface; 194B, densely covered with woolly pubescent hairs 192C.

*Leaf surface*.—Both surfaces; densely pubescent and matte.

*Leaf substance*.—Leathery.

*Petioles*.—Round in shape, strong, average of 4.7 cm in length and 8 mm in diameter, surfaces are densely pubescent and matte, upper surface; 146D, pubescence color 192D, lower surface; 194B, pubescence color 192C and 192D.

*Foliage fragrance*.—Mild mint scent if crushed.

Flower description: No flowers observed to date.

It is claimed:

1. A new and distinct variety of *Senecio* plant named 'Angel Baby' as described and illustrated herein.

* * * * *